US011779532B2

(12) United States Patent
Gan et al.

(10) Patent No.: US 11,779,532 B2
(45) Date of Patent: Oct. 10, 2023

(54) TOPICAL COMPOSITIONS AND METHODS

(71) Applicant: Mary Kay Inc., Addison, TX (US)

(72) Inventors: David Gan, Addison, TX (US); Tiffany Carle, Addison, TX (US)

(73) Assignee: MARY KAY INC., Addison, TX (US)

( * ) Notice: Subject to any disclaimer, the term of this patent is extended or adjusted under 35 U.S.C. 154(b) by 125 days.

(21) Appl. No.: 17/304,013

(22) Filed: Jun. 11, 2021

(65) Prior Publication Data

US 2021/0386646 A1 Dec. 16, 2021

Related U.S. Application Data

(60) Provisional application No. 63/038,499, filed on Jun. 12, 2020.

(51) Int. Cl.
| | | |
|---|---|---|
| *A61K 8/67* | (2006.01) |
| *A61K 8/9717* | (2017.01) |
| *A61K 8/23* | (2006.01) |
| *A61K 8/362* | (2006.01) |
| *A61K 8/55* | (2006.01) |
| *A61Q 19/02* | (2006.01) |
| *A61K 8/9789* | (2017.01) |
| *A61K 8/60* | (2006.01) |

(52) U.S. Cl.
CPC .............. *A61K 8/675* (2013.01); *A61K 8/23* (2013.01); *A61K 8/362* (2013.01); *A61K 8/55* (2013.01); *A61K 8/602* (2013.01); *A61K 8/9717* (2017.08); *A61K 8/9789* (2017.08); *A61Q 19/02* (2013.01); *A61K 2800/524* (2013.01); *A61K 2800/591* (2013.01)

(58) Field of Classification Search
None
See application file for complete search history.

(56) References Cited

U.S. PATENT DOCUMENTS

| | | | |
|---|---|---|---|
| 5,989,596 A | 11/1999 | Bresson-Rival et al. | |
| 6,231,877 B1 | 5/2001 | Vacher et al. | |
| 6,641,845 B1 * | 11/2003 | Kyrou | A61Q 19/00 424/766 |
| 7,226,583 B2 * | 6/2007 | Shepherd, Jr. | A61K 36/605 424/758 |
| 8,784,904 B2 | 7/2014 | Minatelli et al. | |
| 9,364,414 B2 | 6/2016 | Domloge et al. | |
| RE46,228 E | 12/2016 | Cebrian Puche et al. | |
| 9,861,670 B2 | 1/2018 | Clements et al. | |
| 2003/0152536 A1 | 8/2003 | Pauly et al. | |
| 2008/0241084 A1 * | 10/2008 | Siddiqui | A61K 36/45 424/62 |
| 2010/0189662 A1 | 7/2010 | Neubourg | |
| 2010/0247587 A1 * | 9/2010 | Cebrian Puche | A61Q 3/00 424/60 |
| 2012/0177586 A1 | 7/2012 | Mehta et al. | |
| 2014/0377200 A1 * | 12/2014 | Kulesza | A61K 31/192 435/375 |
| 2016/0067163 A1 | 3/2016 | Meyer et al. | |
| 2016/0287505 A1 * | 10/2016 | Rana | A61Q 19/08 |
| 2017/0223997 A1 | 8/2017 | Wang et al. | |
| 2018/0078794 A1 | 3/2018 | Daniels | |
| 2020/0085726 A1 * | 3/2020 | Kalahasti | A61Q 19/02 |

FOREIGN PATENT DOCUMENTS

| | | | | |
|---|---|---|---|---|
| CA | 2823534 A1 * | 7/2012 | | A61K 36/02 |
| WO | WO-9819665 A1 * | 5/1998 | | A61K 8/0295 |
| WO | WO 2014/170239 | 10/2014 | | |
| WO | WO-2016162703 A1 * | 10/2016 | | A23L 33/105 |
| WO | WO 2017/216722 | 12/2017 | | |
| WO | WO 2018/056989 | 3/2018 | | |
| WO | WO 2018/142033 | 8/2018 | | |

OTHER PUBLICATIONS

Hakozaki et al., The effect of niacinamide on reducing cutaneous pigmentation and suppression of melanosome transfer, DOI: 10.1046/j.1365-2133.2002.04834.x, 2002, British Journal of Dermatology, 147, 20-31 (Year: 2002).*
Cha et al., Screening of marine algae for potential tyrosinase inhibitor: Those inhibitors reduced tyrosinase activity and melanin synthesis in zebrafish, DOI: 10.1111/j.1346-8138.2010.00983.x, 2011, Journal of Dermatology, 38, 354-363 (Year: 2011).*
Kardono et al., Development of Papaya Latex, Papaya Extract (*Carica papaya* L.) and Yam Bean Tuber Extract (*Pachyrrhizus erosus* (L.) Urb.) for Skin Lightening Lotion Based on Tyrosinase Inhibition and Antioxidant Activities, ISSN: 1693-1831, 2013, Journal Ilmu Kerarmasian Indonesia, 11(2), 191-196 (Year: 2013).*
Puspaningtyas et al., Evaluation of the effect of red guava (*Psidium guajava*) fruit extract on tyrosinase (EC 1.14.18.1) activity by spectrophotometry, DOI: 10.3329/icpj.v1i5.10280, 2012, International Current Pharmaceutical Journal, 1(5), 92-97 (Year: 2012).*
Narayanaswamy et al., Phytic acid (myo-inositol hexaphosphate)—a promising pharmaceutical agent: A review, DOI: 10.22159/ajpcr.2018.v11i11.27843, 2018, Asian Journal of Pharmaceutical and Clinical Research, 11(11), 42-46 (Year: 2018).*
The 2013 Cosmetic Ingredient Review Expert Panel, Safety Assessment of *Rosmarinus officinalis* (Rosemary)-Derived Ingredients as Used in Cosmetics, https://www.cir-safety.org/sites/default/files/rosmarinus.pdf; accessed Nov. 22, 2022; published Aug. 16, 2013 (Year: 2013).*

(Continued)

*Primary Examiner* — Mark V Stevens
*Assistant Examiner* — Katherine Siller
(74) *Attorney, Agent, or Firm* — NORTON ROSE FULBRIGHT US LLP

(57) ABSTRACT

The present invention relates generally to methods of use and compositions useful to reduce dark spots, age spots, and/or unwanted pigmentation of skin. The composition includes a combination of niacinamide, phytic acid, *Rosmarinus officinalis* leaf extract, *Chondrus crispus* extract, and a combination of *Saxifraga sarmentosa* extract, *Carica papaya* (papaya) fruit extract, and *Psidium guajava* (guava) fruit extract. The composition is effective to reduce dark spots, age spots, and/or unwanted pigmentation of skin. The composition is effective to inhibit tyrosinase and/or Peroxisome Proliferator-Activated Receptor Gamma (PPAR-γ) activity. The composition is further effective to reduce melanin content in skin, particularly dark skin, in some instances by at least 30%.

20 Claims, No Drawings

(56) References Cited

OTHER PUBLICATIONS

Seppic, Beauty Care Ingredient Book, https://www.seppic.com/sites/seppic/files/2018/04/19/2018-seppic_index-beauty-care.pdf, accessed Dec. 1, 2022, published 2018 (Year: 2018).*

Draelos, Active Agents in Common Skin Care Products, PMID: 20124857, 2010, Plast Reconstr Surg, 125(2), 719-724. (Year: 2010).*

Sakamoto et al., Cosmetic Science and Technology: Theoretical Principles and Applications, ISBN: 978-0-12-802005-0, 2017, Elsevier Inc., 231-244 (Year: 2017).*

Jarchem Industries, Inc., Sucranov ™ Sugar Based Surfactants, https://www.jarchem.com/wp-content/uploads/2017/05/JII-Sucranov-Surfactants-20170427.pdf, accessed Nov. 30, 2022 (Year: 2022).*

SpecialChem, Caprylyl/Capryl Glucoside, https://cosmetics.specialchem.com/inci-ingredients/caprylyl-capryl-glucoside, accessed Nov. 28, 2022 (Year: 2022).*

Katoulis et al., A randomized double blind vehicle-controlled study of a preparation containing Undecylenoyl Phenylalanine 2% in the treatment of solar lentigines, PMID: 24910270, 2009, J Cosmet Dermatol., 4, 69-72. (Year: 2009).*

The 2020 Cosmetic Ingredient Review Expert Panel, Safety Assessment of *Carica papaya* (Papaya)-Derived Ingredients as Used in Cosmetics, https://www.cir-safety.org/sites/default/files/Papaya.pdf, accessed Nov. 22, 2022, released Feb. 21, 2020 (Year : 2020).*

Integrated Taxonomic Information System, *Saxifraga sarmentosa* L.f., https://www.itis.gov/servlet/SingleRpt/SingleRpt7search_topic=TSN&search_value=24295#null, accessed Nov. 30, 2022 (Year: 2022).*

Knowde, Glycolysat® of Papaya UP, https://www.knowde.com/stores/solabia-group/products/glycolysat-of-papaya-up, accessed Dec. 1, 2022 (Year: 2022).*

MatTek, MelanoDerm™, https://www.mattek.com/products/melanoderm/, accessed Dec. 1, 2022 (Year: 2022).*

Castanedo-Cazares et al., Topical niacinamide 4% and desonide 0.05% for treatment of axillary hyperpigmentation: a randomized, double-blind, placebo-controlled study, PMID: 23355788, 2013, Clinical, Cosmetic and Investigational Dermatology, 6, 29-36 (Year: 2013).*

International Search Report and Written Opinion issued in Corresponding PCT Application No. PCT/US2021/070700, dated Oct. 29, 2021.

* cited by examiner

TOPICAL COMPOSITIONS AND METHODS

CROSS-REFERENCE TO RELATED APPLICATIONS

This application claims the benefit of priority to U.S. Provisional Patent Application Ser. No. 63/038,499, filed Jun. 12, 2020, hereby incorporated by reference in its entirety.

BACKGROUND OF THE INVENTION

A. Field of the Invention

The present invention relates generally to various skin formulations that are structured in such a way to treat a wide range of skin conditions related to unwanted pigmentation of aging skin. The formulations can be used separately or in combination in a regimen format.

B. Description of Related Art

The color in human skin is caused by the pigment melanin. Melanogenesis is the process by which special dendritic cells, melanocytes, produce melanin. Melanocytes are found below or between the basal cells of the epidermis of the skin. Many individuals have excess melanin pigmentation or a hyperpigmentation patch in the skin, which can cause pigmentary variation or abnormal pigmentation of the skin. This can lead to unwanted freckles or dark spots such as senile lentigo, liver spots, melasma, brown or age spots, vitiligo, sunburn pigmentation, post-inflammatory hyperpigmentation due to abrasion, burns, wounds or dermatitis, phototoxic reaction and other similar small, fixed pigmented lesions.

It is often desirable to lighten these areas or even out the appearance of irregularly pigmented areas of skin to provide a more even looking skin tone/skin color. Individuals may also wish to increase the fairness of or reduce the overall level of pigmentation in the skin. In either case, the hyperpigmentation is usually viewed as cosmetically undesirable and individuals often wish to lighten the skin.

Many factors contribute to increased pigmentation of the skin such as the actual age of a person, the amount of exposure to environmental factors (e.g., sun light, pollution, chemicals, smoke, etc.), and how well a person has protected their skin. In particular, increased pigmentation of skin concerns two processes—intrinsic aging, which is related to the natural aging process and genetic influences, and extrinsic, or accumulated damage due to environmental factors such as sun exposure.

Extrinsic factors can cause keratinocytes (the outermost cells of the skin) to release signaling molecules, such as α-melanocyte-stimulating hormone (α-MSH) and inflammatory cytokines, each of which can lead to unwanted skin pigmentation and/or skin inflammation (e.g., reddened and/or erythemic skin). Extrinsic factors can also cause up-regulation of the gene for tyrosinase, which is known to catalyze two steps in the multi-step biosynthesis of melanin pigments. Further, Peroxisome Proliferator-Activated Receptor Gamma (PPAR-γ) agonists may be increased. PPAR-γ is known to increase melanin production by stimulating tyrosinase activity and expression. PPAR-γ agonists are also known to stimulate migration of melanocytes in skin.

The combination of intrinsic aging and extrinsic factors not only can increase pigmentation in skin, but can also eventually lead to visible signs of skin aging. The early signs of skin aging include the beginning of uneven skin tone. Typically, this occurs in an age range of about 25 to 35 years of age. The moderate signs of skin aging include the appearance of more significant age spots and areas of hyperpigmentation. This typically occurs in an age range of about 35 to 50 years of age. The advanced signs of skin aging include more prominent dark spots which may grow in size and group together to give the skin a speckled or more mottled appearance. Typically this occurs in an age range of above 50 years of age.

Various skin lightening ingredients are known which inhibit melanogenesis to prevent skin darkening and to lighten dark spots associated with aging. In some instances, the use of one skin lightening ingredient may not be effective for individuals with significant hyperpigmentation, freckles, or age spots, for example. Additionally, many previous attempts to combine various skin lightening ingredients have been ineffective, and in some instance, have produced negative results such as exasperating the production of inflammatory cytokines. Further, certain skin lightening ingredients, such as hydroquinone, are known to increase hyperpigmentation in darker skin tones.

SUMMARY OF THE INVENTION

The inventors have identified a solution to at least some of the problems associated with unwanted skin pigmentation. In some instances, the inventors have discovered a unique set of ingredients that can be used to treat unwanted pigmentation of skin, particularly dark spots and/or age spots. Finally, the ingredients and formulations thereof are as effective or more effective than other known skin lightening ingredients (e.g., kojic acid or hydroquinone). The solution is premised on a discovery of a combination of ingredients that can work together to modify certain biochemical pathways in the skin to reduce pigmentation. Without being bound by theory, this combination of ingredients is believed to inhibit PPAR-γ and/or tyrosinase, which inhibits melanogenesis. This combination can include an effective amount of niacinamide, ferulic acid, tetrahexyldecyl ascorbate, phytic acid, *Rosmarinus officinalis* leaf extract, *Schinus terebinthifolius* seed extract, *Chondrus crispus* extract, *Saxifraga sarmentosa* extract, *Carica papaya* (papaya) fruit extract, *Psidium guajava* fruit extract, undecylenoyl phenylalanine, *Pfaffia paniculata* root extract, *Ptychopetalum olacoides* bark/stem extract, and/or *Trichilia catigua* extract to inhibit PPAR-γ and/or tyrosinase activity, reduce dark spots, reduce age spots, and/or reduce unwanted pigmentation.

In particular, it was discovered that this combination of ingredients has the ability to reduce dark spots, age spots, and/or unwanted pigmentation in skin. In certain aspects, it was discovered that this combination of ingredients has the ability to reduce the overall melanin level in skin. In certain aspects, this combination has the ability to reduce the overall melanin level in skin by at least 5%, 10%, 15%, 20%, 25%, 30%, or more. In certain aspects, this combination has the ability to reduce the overall melanin level in dark skin. In certain aspects, this combination has the ability to reduce the overall melanin level content in dark skin by at least 5%, 10%, 15%, 20%, 25%, 30%, or more. In certain aspects, the skin is of a person with a brown or black complexion. In certain aspects, the skin is of a person with a black complexion.

In some aspects there is disclosed a topical skin composition. In some instances, there is disclosed a topical skin composition including an effective amount of niacinamide, ferulic acid, tetrahexyldecyl ascorbate, phytic acid, *Rosmarinus officinalis* leaf extract, *Schinus terebinthifolius* seed extract, *Chondrus crispus* extract, *Saxifraga sarmentosa* extract, *Carica papaya* (papaya) fruit extract, *Psidium guajava* fruit extract, undecylenoyl phenylalanine, *Pfaffia paniculata* root extract, *Ptychopetalum olacoides* bark/stem extract, and/or *Trichilia catigua* extract to reduce dark spots, age spots, and/or unwanted pigmentation.

In certain aspects, the topical skin composition includes a combination of *Saxifraga sarmentosa* extract, *Carica papaya* (papaya) fruit extract, and *Psidium guajava* fruit extract. In certain aspects, the combination of *Saxifraga sarmentosa* extract, *Carica papaya* (papaya) fruit extract, and *Psidium guajava* fruit extract may further include sodium sulfite and sodium metabisulfite. In certain aspects, the combination of *Saxifraga sarmentosa* extract, *Carica papaya* (papaya) fruit extract, and *Psidium guajava* fruit extract may further include an effective amount of sodium sulfite and sodium metabisulfite to reduce dark spots, age spots, and/or unwanted pigmentation.

In certain aspects, the topical skin care composition includes a combination of *Saxifraga sarmentosa* extract, *Carica papaya* (papaya) fruit extract, and *Psidium guajava* fruit extract, *Pfaffia paniculata* root extract, *Ptychopetalum olacoides* bark/stem extract, and *Trichilia catigua* extract. In certain aspects, the combination of *Saxifraga sarmentosa* extract, *Carica papaya* (papaya) fruit extract, and *Psidium guajava* fruit extract, *Pfaffia paniculata* root extract, *Ptychopetalum olacoides* bark/stem extract, and *Trichilia catigua* extract may further include glycerin and caprylyl/capryl glucoside. In certain aspects, the combination of *Saxifraga sarmentosa* extract, *Carica papaya* (papaya) fruit extract, and *Psidium guajava* fruit extract, *Pfaffia paniculata* root extract, *Ptychopetalum olacoides* bark/stem extract, *Trichilia catigua* extract, glycerin, and caprylyl/capryl glucoside is provided in an amount of 0.1 to 5% w/w. In further aspects, the combination of *Pfaffia paniculata* root extract, *Ptychopetalum olacoides* bark/stem extract, *Trichilia catigua* extract, glycerin, and caprylyl/capryl glucoside is provided in an amount of 0.5% w/w.

In some aspects, the topical skin composition has the ability to inhibit tyrosinase and/or PPAR-γ activity. In some aspects, the *Rosmarinus officinalis* leaf extract has the ability to inhibit tyrosinase and/or PPAR-γ activity. In some aspects, the topical skin composition is effective to reduce dark spots, age spots, and/or unwanted pigmentation of skin. In some aspects, the topical skin composition is effective to reduce the overall melanin level in skin. In some instances, the topical skin composition is effective to reduce the overall melanin level in skin by at least 5%, 10%, 15%, 20%, 25%, 30%, or more. In certain aspects, the topical skin composition has the ability to reduce the overall melanin level in dark skin. In certain aspects, the topical skin composition has the ability to reduce the overall melanin level in dark skin by at least 5%, 10%, 15%, 20%, 25%, 30%, or more. In certain aspects, the skin is of a person with a brown or black complexion. In certain aspects, the skin is of a person with a black complexion.

In some instances, the topical composition includes 0.1 to 10% w/w of niacinamide, 0.01 to 1% w/w of ferulic acid, 0.1 to 5% w/w of tetrahexyldecyl ascorbate, 0.01 to 3% w/w of phytic acid, 0.1 to 5% w/w of *Rosmarinus officinalis* leaf extract, 0.01 to 3% w/w of *Schinus terebinthifolius* seed extract, 0.1 to 5% w/w of *Chondrus crispus* extract, 0.1 to 5% w/w of a combination of *Saxifraga sarmentosa* extract, *Carica papaya* (papaya) fruit extract, and *Psidium guajava* fruit extract, and 0.1 to 5% w/w of undecylenoyl phenylalanine. In some instances, the topical composition includes 0.1 to 5% w/w of a combination of *Pfaffia paniculata* root extract, *Ptychopetalum olacoides* bark/stem extract, *Trichilia catigua* extract, glycerin, and caprylyl/capryl glucoside In some instances, the *Rosmarinus officinalis* leaf extract is an extract of deep eutectic solvent comprising lactic acid, betaine, and water. In some instances, the *Schinus terebinthifolius* seed extract is a supercritical $CO_2$ extract. In some instances, the *Chondrus crispus* extract is an aqueous extract. In some instances, the *Saxifraga sarmentosa*, *Carica papaya* (papaya) fruit, and *Psidium guajava* fruit extracts are hydroglycolic extracts.

It is contemplated that any embodiment discussed in this specification can be implemented with respect to any method or composition of the invention, and vice versa. Furthermore, compositions of the invention can be used to achieve methods of the invention.

In the context of the present invention, at least the following 21 aspects are described. Aspect 1 includes a method of reducing dark spots, age spots, and/or unwanted pigmentation of skin. The method comprises topically applying to dark spots, age spots, and/or unwanted pigmentation a skin care composition comprising an effective amount of niacinamide, ferulic acid, tetrahexyldecyl ascorbate, phytic acid, *Rosmarinus officinalis* leaf extract, *Schinus terebinthifolius* seed extract, *Chondrus crispus* extract, *Saxifraga sarmentosa* extract, *Carica papaya* (papaya) fruit extract, *Psidium guajava* fruit extract, and undecylenoyl phenylalanine to reduce dark spots, age spots, and/or unwanted pigmentation of skin. Aspect 2 depends on Aspect 1, wherein the skin care composition further comprises sodium sulfite and sodium metabisulfite. Aspect 3 depends on Aspect 2, wherein the skin care composition comprises an effective amount of sodium sulfite and sodium metabisulfite to reduce dark spots, age spots, and/or unwanted pigmentation of skin. Aspect 4 depends on any of Aspects 1 to 3, wherein the skin care composition comprises 0.1 to 10% by weight of niacinamide, 0.01 to 1% by weight of ferulic acid, 0.1 to 5% by weight of tetrahexyldecyl ascorbate, 0.01 to 3% by weight of phytic acid, 0.1 to 5% by weight of *Rosmarinus officinalis* leaf extract, 0.01 to 3% by weight of *Schinus terebinthifolius* seed extract, 0.1 to 5% by weight of *Chondrus crispus* extract, 0.1 to 5% w/w of a combination of *Saxifraga sarmentosa* extract, *Carica papaya* (papaya) fruit extract, and *Psidium guajava* fruit, and 0.1 to 5% by weight of undecylenoyl phenylalanine. Aspect 5 depends on any of Aspects 1 to 4, wherein the *Rosmarinus officinalis* leaf extract is an extract of deep eutectic solvent comprising lactic acid, betaine, and water, the *Schinus terebinthifolius* seed extract is a supercritical $CO_2$ extract, the *Chondrus crispus* extract is an aqueous extract, the *Saxifraga sarmentosa* is a hydroglycolic extract, *Carica papaya* (papaya) fruit is a hydroglycolic extract, and/or *Psidium guajava* fruit extract is a hydroglycolic extract. Aspect 6 depends on any of Aspects 1 to 5, wherein topical application of the composition reduces the overall melanin level of skin. Aspect 7 depends on any of Aspects 1 to 6, wherein topical application of the composition reduces the overall melanin level of skin by at least 5%, 10%, 15%, 20%, 25%, or 30%. Aspect 8 depends on any of Aspects 1 to 7, wherein topical application of the composition reduces the overall melanin level of dark skin by at least 30%. Aspect 9 depends on any of Aspects 1 to 8, wherein the skin is of a person with a brown or black complexion. Aspect 10 depends on Aspect 9, wherein the skin is of a person with a black complexion.

Aspect 11 depends on any of Aspects 1 to 10, wherein topical application of the composition inhibits tyrosinase and/or Peroxisome Proliferator-Activated Receptor Gamma (PPAR-γ) activity of the skin. Aspect 12 includes a skin care composition comprising an effective amount of niacinamide, ferulic acid, tetrahexyldecyl ascorbate, phytic acid, *Rosmarinus officinalis* leaf extract, *Schinus terebinthifolius* seed extract, *Chondrus crispus* extract, *Saxifraga sarmentosa* extract, *Carica papaya* (papaya) fruit extract, *Psidium guajava* fruit extract, and undecylenoyl phenylalanine to reduce dark spots, age spots, and/or unwanted pigmentation of skin. Aspect 13 depends on Aspect 12, wherein the skin care composition further comprises sodium sulfite and sodium metabisulfite. Aspect 14 depends on Aspect 13, wherein the skin care composition comprises an effective amount of sodium sulfite and sodium metabisulfite to reduce dark spots, age spots, and/or unwanted pigmentation of skin. Aspect 15 depends on any of Aspects 12 to 14, wherein the composition comprises 0.1 to 10% by weight of niacinamide, 0.01 to 1% by weight of ferulic acid, 0.1 to 5% by weight of tetrahexyldecyl ascorbate, 0.01 to 3% by weight of phytic acid, 0.1 to 5% by weight of *Rosmarinus officinalis* leaf extract, 0.01 to 3% by weight of *Schinus terebinthifolius* seed extract, 0.1 to 5% by weight of *Chondrus crispus* extract, 0.1 to 5% w/w of a combination of *Saxifraga sarmentosa* extract, *Carica papaya* (papaya) fruit extract, and *Psidium guajava* fruit, and 0.1 to 5% by weight of undecylenoyl phenylalanine. Aspect 16 depends on any of Aspects 12 to 15, wherein the *Rosmarinus officinalis* leaf extract is an extract of deep eutectic solvent comprising lactic acid, betaine, and water, the *Schinus terebinthifolius* seed extract is a supercritical $CO_2$ extract, the *Chondrus crispus* extract is an aqueous extract, the *Saxifraga sarmentosa*, is a hydroglycolic extract, the *Carica papaya* (papaya) fruit is a hydroglycolic extract, and the *Psidium guajava* fruit extract is a hydroglycolic extract. Aspect 17 depends from any of Aspects 12 to 16, wherein the composition is effective to reduce the overall melanin level of skin. Aspect 18 depends from any of Aspects 12 to 17, wherein the composition is effective to reduce the overall melanin level of skin by at least 5%, 10%, 15%, 20%, 25%, or 30%. Aspect 19 depends from any of Aspects 12 to 18, wherein the composition is effective to reduce the overall melanin level of dark skin by at least 30%. Aspect 20 depends from any of Aspects 12 to 19, wherein the skin is of a person with a brown or black complexion. Aspect 21 depends from Aspect 20, wherein the skin is of a person with a black complexion.

In some instances, the topical skin composition is used in a method to reduce pigmentation. In some instances, the topical skin composition is used to inhibit tyrosinase. In some instances, the topical skin composition is used to inhibit PPAR-γ activity. In some instances, the topical skin composition is used to reduce dark spots, age spots, and/or unwanted pigmentation of skin. In some instances, the topical skin composition is used to reduce the overall melanin level in skin by at least 5%, 10%, 15%, 20%, 25%, 30%, or more. In some instances, the topical skin composition is used to reduce the overall melanin level in dark skin. In some instances, the topical skin composition is used to reduce the overall melanin level in dark skin by at least 5%, 10%, 15%, 20%, 25%, 30%, or more. In certain aspects, the skin is of a person with a brown or black complexion. In certain aspects, the skin is of a person with a black complexion.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

In some embodiments, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a serum, a gel, a wash, a body butter, a scrub, a foundation, a night cream, a lipstick, a cleanser, a toner, a sunscreen, a mask, an anti-aging product, a deodorant, an antiperspirant, a perfume, a cologne, etc.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase, such as a measurable increase of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," it is expected that a basic and novel property of the compositions and methods of the present invention will be the ability to reduce dark spots, age spots, and/or unwanted pigmentation of skin and/or inhibit tyrosinase and/or PPAR-γ activity in skin. Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, the present invention provides a solution to the problems associated with current cosmetic products. In some embodiments, the composition includes an effective amount of any one of, any combination of, or all of niacinamide, ferulic acid, tetrahexyldecyl ascorbate, phytic acid, *Rosmarinus officinalis* leaf extract, *Schinus terebinthifolius* seed extract, *Chondrus crispus* extract, *Saxifraga sarmentosa* extract, *Carica papaya* (papaya) fruit extract, *Psidium guajava* fruit extract, and undecylenoyl phenylalanine to reduce dark spots, age spots, and/or unwanted pigmentation of skin and/or inhibit tyrosinase and/or PPAR-γ activity. In certain aspects, this combination of ingredients is effective to reduce the overall melanin level in skin. In certain aspects, this combination is effective to reduce the overall melanin level in skin by at least 5%, 10%, 15%, 20%, 25%, 30%, or more. In certain aspects, this combination is effective to reduce the overall melanin level in dark skin. In certain aspects, this combination is effective to reduce the overall melanin level content in dark skin by at least 5%, 10%, 15%, 20%, 25%, 30%, or more.

A. Active Ingredients

The combination of ingredients can be used in different product forms to treat various skin conditions. By way of non-limiting examples, the combination of ingredients can be formulated in an ampule, an emulsion (e.g., oil in water, water in oil), a gel, a serum, a gel emulsion, a gel serum, a lotion, a mask, a scrub, a wash, a cream, or a body butter.

Niacinamide:

Also known as nicotinamide, 3-Pyridinecarboxamide, or Vitamin B3, niacinamide is an organic compound known to exhibit skin conditioning benefits when used in cosmetic compositions. Niacinamide has the following chemical formula:

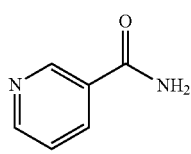

It has been discovered that niacinamide can be used to provide added skin brightening benefits and to inhibit melanin transfer to the skin. This ingredient is commercially available from a variety of sources.

Ferulic Acid:

Also known as 4-hydroxy-3-methoxy-cinnamic acid, ferulic acid is a plant-based organic compound exhibiting skin protecting benefits when used in cosmetic compositions. Ferulic acid has the following chemical formula:

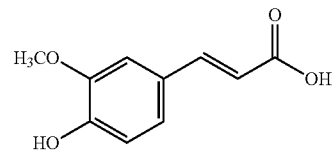 [SMILES: COc1cc(/C=C/C(=O)O)ccc1O]

This ingredient is commercially available from a variety of sources. It has been discovered that ferulic acid ingredient is a powerful antioxidant capable of stabilizing solutions of vitamins C and E for topical applications. Synergistic benefits of such combinations have been shown to protect the skin from photoaging and skin cancer caused by solar irradiation. Further, ferulic acid is capable of inhibiting melanin production in skin by competitively binding to tyrosinase.

Tetrahexyldecyl Ascorbate:

Also known as ascorbyl tetraisopalmitate, tetrahexyldecyl ascorbate is a vitamin C derivative that functions as an antioxidant and skin conditioner agent. Tetrahexyldecyl ascorbate is commercially available and can be obtained from Nikko under the trade names NIKKOL BV-OSC.

Phytic Acid:

Also known as inositol hexakisphosphate (IP6) or inositol polyphosphate, phytic acid is a plant-based, six-fold dihydrogenphosphate ester of the myo isomer of inositol. At physiological pH, the phosphates are partially ionized, resulting in the phytate anion. Phytic acid has the following chemical structure:

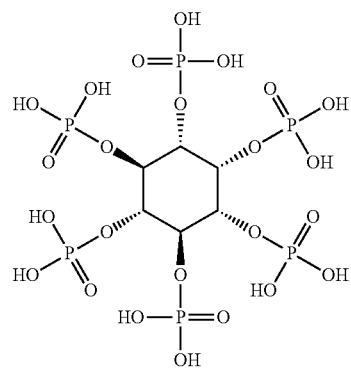 [SMILES: O=P(O)(O)O[C@H]1[C@H](OP(=O)(O)O)[C@@H](OP(=O)(O)O)[C@H](OP(=O)(O)O)[C@@H](OP(=O)(O)O)[C@H]1OP(=O)(O)O]

Phytic acid is a powerful antioxidant. Phytic acid is capable of scavenging free radicals that contribute to the formation of premature wrinkles and fine lines on the skin. Phytic acid also inhibits melanin production by chelating iron and copper which are necessary for the formation of melanin. Phytic acid can reduce unwanted pigmentation and dark spots of the skin associated with aging and exposure to UV light.

*Rosmarinus officinalis* Leaf Extract:

*Rosmarinus officinalis* leaf extract is an extract from the leaf of *Rosmarinus officinalis*. *Rosmarinus officinalis* is native to the Mediterranean region, and is a woody, perennial herb with fragrant, evergreen, needle-like leaves and white, pink, purple, or blue flowers. It is a shrub that can reach up to 1.5 meters in height with leaves that are about 2 to 4 cm long with green (top surface) and white (bottom surface) coloring. The leaf can be subjected to a eutectigenesis extraction process using a fluid extraction mixture comprising betaine or hydrated betaine, a hydrogen bond donor compound (e.g., polyols, organic acids, etc.), and water. In particular, the leaf portion can be crushed or macerated and then subjected to the aforementioned eutectic fluid extraction mixture to obtain a eutectic extract. The eutectic extract can then be used in the compositions of the present invention. In some preferred instances, the hydrogen bond donor is an organic acid, preferably lactic acid. Eutectigenesis utilizes eutectic solvents which are mixtures of compounds having melting points lower than those of their constituents taken in isolation. In some instances, *Rosmarinus officinalis* extract is commercially available. In some instances, *Rosmarinus officinalis* extract can be an extract of a deep eutectic solvent comprising lactic acid, betaine, and water, supplied by Naturex (France) under the trade name ROSEMARY EUTECTYS® BLA.

*Schinus terebinthifolius* Seed Extract:

*Schinus terebinthifolius* seed extract is an extract from the seed of a flowering plant of the Anacardiaceae (cashew) family, which is located primarily in subtropical and tropical South America. In some instances, *Schinus terebinthifolius* seed extract is commercially available. In some instances, *Schinus terebinthifolius* seed extract can be supplied by Barnet Products Corporation under the trade name ADIPOLIN®. In a preferred instance, $CO_2$ supercritical extraction can be used to obtain the *Schinus terebinthifolius* seed extract. $CO_2$ supercritical extraction can include filling a column with ground dried plant material and pumping supercritical liquid carbon dioxide though the column at very high pressure (200-400 Bar), and then collecting the resulting extract.

*Chondrus crispus* Extract:

*Chondrus crispus* extract is an extract of the red algae, *Chondrus crispus*. *Chondrus crispus* is rich in minerals, particularly iodine and sulfur. *Chondrus crispus* extract is used as a skin conditioning agent as well as a viscosity modifier for topical skin formulations. In some instances, *Chondrus crispus* extract can be an aqueous extract supplied by Biotech Marine (Seppic) under the trade name OLIGOGELINE® PF.

*Saxifraga sarmentosa* Extract:

*Saxigraga sarmentosa* extract is an extract of the flowering herb strawberry begonia, *Saxifraga sarmentosa*. In skin care products, *Saxifrage sarmentosa* extract functions as a skin conditioning agent, an antimicrobial agent, and an astringent. *Saxifraga sarmentosa* extract is suggested to have skin lightening properties.

*Carica papaya* (*Papaya*) Fruit Extract:

*Carica papaya* (papaya) fruit extract is an extract of the fruit of the papaya, *Carica papaya*. *Carica papaya* (papaya) fruit extract is a skin conditioning agent. *Papaya* contains the proteolytic enzyme papain which speeds wound healing and accelerates new tissue growth when applied to the skin.

*Psidium guajava* Fruit Extract:

Guava or *Psidium guajava* is an evergreen tree or shrub that can reach 6 to 25 feet in height. It produces green leaves, fragrant white flowers, and pear-shaped fruit. Guava fruit is rich in vitamins A, B, and C, tannins, phenolic compounds, and flavonoids. *Psidium guajava* fruit extract is used as a skin conditioning agent and astringent. This ingredient is also suggested to have antimicrobial and skin repair properties.

In some instances, a blend of *Saxifraga sarmentosa* extract, *Carica papaya* (*Papaya*) fruit extract, and *Psidium guajava* fruit extract is used, supplied by BASF Care Chemicals, Florham Park, N.J. (USA) under the trade name DERMAWHITE® WF. This hydroglycol formulation of plant extracts is supplied in a mixture of water, glycerin, and butylene glycol. This formulation further includes sodium sulfite and sodium metabisulfite. Sodium sulfite and sodium metabisulfite may possibly also inhibit melanogenesis. See U.S. Pat. No. 5,989,596.

Undecylenoyl Phenylalanine:

Undecylenoyl phenylalanine is a substituted amino acid capable of lightening the skin. Undecylenoyl phenylalanine has the following structure:

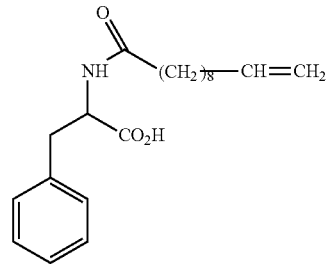

In some instances, undecylenoyl phenylalanine can be supplied by Seppic under the trade name SEPIWHITE® MSH.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, deep eutectic solvents, heat, pressure, pressure drop extraction, ultrasonic extraction, etc. Extracts can be a liquid, solid, dried liquid, re-suspended solid, etc.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and a wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, scrubs, body butters, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, gluconolactone, calcium gluconate, cyclohexasiloxane, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (Carthamus tinctorius) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (Carthamus tinctorius) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include sodium cocoyl glutamate, hydroxypropyl cyclodextrin, stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (see U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oil such as a polyorganosiloxane. Non-limiting examples of polyorganosiloxanes include dimethicone, cyclomethicone, cyclohexasiloxane, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e., normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e., dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, a hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/VP copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerythritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Exemplary Formulations

Formulations having the ingredients disclosed herein were prepared as topical skin compositions. In some instances, the topical skin compositions can be prepared as an ampule, serum, cream, emulsion, gel, or gel emulsion. The formulation in Table 1 is an example of a topical skin composition.

TABLE 1^

| Ingredient | % Concentration (by weight) |
| --- | --- |
| Niacinamide | 3 |
| Ferulic acid | 0.3 |
| Tetrahexyldecyl ascorbate | 2 |
| Phytic Acid | 0.5 |
| *Rosmarinus officinalis* leaf extract | 2 |
| *Schinus terebinthifolius* seed extract | 0.5 |
| *Chondrus crispus* extract | 1 |
| *Saxifraga sarmentosa* extract and *Carica papaya* (papaya) fruit extract and *Psidium guajava* fruit extract* | 2 |
| Undecylenoyl phenylalanine | 2 |
| Excipients** | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*This combination of extracts can also contain Sodium sulfite and Sodium bisulfite.
**Excipients can be added, for example, to modify the rheological properties of the composition. Alternatively, the amount of water can be varied.

The formulation in Table 2 is an example of a topical skin composition.

TABLE 2

| Ingredient | % Concentration (by weight) |
| --- | --- |
| Dimethyl isosorbide | 6 |
| Dimethicone | 5 |
| Pentylene glycol | 4 |
| Niacinamide | 3 |
| Glycerin | 2.4 |
| Silica | 2 |
| Ammonium acryloyldimethyl taurate/VP copolymer | 1.5 |
| Lactic acid | 0.8 |
| Betaine | 0.7 |
| Potassium hydroxide | 0.6 |
| Phenoxyethanol | 0.5 |
| Acrylates/C10-30 alkyl acrylate crosspolymer | 0.3 |
| Polysorbate 20 | 0.3 |
| Caprylyl glycol | 0.1 |
| Disodium EDTA | 0.1 |
| Vegetable amino acids | 0.1 |
| Xanthan gum | 0.1 |
| Decylene glycol | 0.08 |
| Citric acid | 0.05 |
| 1,2-hexanediol | 0.04 |
| Ethylhexylglycerin | 0.04 |
| Hexylene glycol | 0.04 |
| *Rosmarinus officinalis* leaf extract | 0.04 |
| Excipients* | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*Excipients can be added, for example, to modify the rheological properties of the composition. Alternatively, the amount of water can be varied.

Example 2

Materials Used

Active ingredients in Table 3 were used to prepare the formulations of Tables 1 and 2.

TABLE 3

| Ingredient |
| --- |
| Niacinamide, supplied by DSM |
| Ferulic acid, supplied by Kinetic |
| Tetrahexyldecyl ascorbate, supplied by Nikko under the tradename NIKKOL ® BV-OSC |
| Phytic Acid supplied by Biosil |
| *Rosmarinus officinalis* leaf extract, supplied by Naturex under the tradename ROSEMARY EUTECTYS ® BLA |
| *Schinus terebinthifolius* seed extract, supplied by Barnet under the tradename ADIPOLIN ® |
| *Chondrus crispus* extract, supplied by Marine Biotech under the trademane OLIGOGELINE ® PF |
| *Saxifraga sarmentosa* extract and *Carica papaya* (papaya) fruit extract, *Psidium guajava* fruit extract, sodium sulfite, and sodium bisulfite, supplied by BASF under the tradename DERMAWHITE WF |
| *Pfaffia Paniculata* root extract, *Ptychopetalum Olacoides* Bark/Stem extract, and *Trichilia Catigua* extract, supplied by Chemyunion under the tradename SLIMBUSTER H3R |
| Undecylenoyl phenylalanine, supplied by Seppic under the tradename SEPIWHITE ® MSH |

Example 3

In-Vitro Assays for Melanin Level

A formulation containing the ingredients in Table 1 was used to determine Overall Melanin Level.

Overall Melanin Level Assay:

This bioassay was used to analyze the effect of compounds on melanogenesis. The topical application to skin of the combination of compounds of Table 1 significantly reduced melanin production and macroscopic darkening compared to untreated controls. The endpoint of this assay was spectrophotometric measurement of melanin production and cellular viability of tissue constructs derived from donors.

The skin lightening efficacy of the formulation in Table 1 was evaluated using a skin analog sold by MatTek Corp. under the tradename MELANODERM™. Tissue constructs derived from donors with a black complexion (MELANODERM™ MEL-300B) were used. Tissue constructs derived from people with a black complexion have melanocytes with increased pigmentation versus those of people with a white or brown complexion melanocytes. MEL-300B tissue inserts were placed into the wells of 12-well plates filled with maintenance medium and pre-equilibrated in a humidified 37° C., 5% $CO_2$ incubator overnight prior to applying treatment. After removal of the pre-equilibration medium, 25 µl of the formulation of Table 1 was applied directly to the MEL-300B stratum corneum by pipetting with a positive displacement pipette into the cell culture insert which contained the MEL-300B tissue inserts. Treatments were done in triplicates. 25 µl of 2% Kojic Acid (KA) solution and 25 µl of 0.4% Hydroquinone (HQ) solution were used as positive controls and 25 µl of sterile ultrapure water served as negative control.

The MEL-300B tissue inserts were treated every other day for 10 consecutive days. Maintenance medium was replaced every other day with fresh medium. After treatment, the MEL-300B tissue inserts were submerged in phosphate buffered saline (PBS) for 10 minutes to remove any residual phenol red and test article from the tissue. After the MEL-300B tissue inserts were rinsed off, viability was measured on one of the tissues using the MTT viability assay (MTT Kit part #: MTT-100).

The relative melanin content was measured using the Solvable Melanin Assay. Briefly, the tissues were removed from the inserts using fine-point forceps. Each tissue was blotted dry and placed in a 1.7 ml microfuge tube. 500 µl of SOLVABLE™ (Tissue and Gel Solubilizer 0.5 M—Packard BioScience Co. Catalogue No. 6NE9100) was added to each tube such that each tissue was completely submerged. The tubes were closed and incubated at 95° C. in a water bath for 2 hrs. The samples were Vortexed until the membranes were completely dissolved. After cooling, 200 µl of the sample was pipetted into each well of a 96 well plate. Absorbance of the plate was read at 490 nM.

Table 4 below shows the absorbance values for the untreated control compared to the 2% kojic acid solution, 0.4% hydroquinone, and the formulation of Table 1. Treatment of MEL-300B tissue with the formulation of Table 1 reduced the overall melanin level in the MEL-300B tissue construct by 31.93% compared to the untreated control. Further, the formulation of Table 1 was shown to be equally as effective as kojic acid, a known melanogenesis inhibitor. Finally, the formulation of Table 1 was effective for dark skin, unlike the hydroquinone treatment, which was shown to increase melanin compared to the untreated control.

TABLE 4

| Test Solution | Absorbance |
| --- | --- |
| Untreated | 0.927 |
| Kojick Acid | 0.629 |
| Hydroquinone | 1.222 |
| Formula of Table 1 | 0.631 |

In a related test, a combination of *Pfaffia paniculata* root extract, *Ptychopetalum olacoides* bark/stem extract, and *Trichilia catigua* extract was evaluated using the MELANODERM™ system. A net 0.05 wt. % solution of these ingredients provided a reduction in overall melanin level of 17%.

Example 5

In-Vitro Assays for PPAR-γ Antagonism

*Rosmarinus officinalis* leaf extract, supplied by Naturex under the tradename ROSEMARY EUTECTYS® BLA listed in Table 2 was used to determine PPAR-γ Antagonism.

PPAR-γ Antagonist Assay (NHR Assay):

PPAR-γ is a receptor critical for the production of melanin. The activity of PPAR-γ was determined using a Nuclear Hormone Receptor Assay (NHR) in antagonist mode that analyzed the ability of *Rosmarinus officinalis* leaf extract, supplied by Naturex under the tradename ROSEMARY EUTECTYS® BLA to inhibit binding of a ligand to PPAR-γ. Briefly, PATHHUNTER® NHR Protein Interaction (Pro) Assay was used to monitor the activation of PPAR-γ in a homogenous, non-imaging assay format using Enzyme Fragment Complementation (EFC). The NHR Pro assay is based on detection of protein-protein interactions between an activated, full length NHR protein and a nuclear fusion protein containing Steroid Receptor Co-activator Peptide (SRCP) domains with one or more canonical interaction motifs. The NHR is tagged with the PROLINK™ component of the EFC assay system, and the SRCP domain is fused to the enzyme acceptor component (EA) expressed in the nucleus. When bound by ligand, the NHR will migrate to the nucleus and recruit the SRCP domain, whereby complementation occurs, generating a unit of active β-Galactosidase (β-Gal) and production of chemiluminescent signal.

PathHunter NHR cell lines were expanded from freezer stocks according to standard procedures. Cells were seeded in a total volume of 20 µL into white walled, 384-well microplates and incubated at 37° C. for the appropriate time prior to testing. Assay media contained charcoal-dextran filtered serum to reduce the level of hormones present. For antagonist determination, cells were pre-incubated with antagonist followed by agonist challenge at the EC80 concentration. Intermediate dilution of sample stocks was performed to generate 5× sample in assay buffer. 5 µL of 5× sample was added to cells and incubated at 37° C. or room temperature for 60 minutes. Vehicle concentration was 1%. 5 µL of 6× EC80 agonist in assay buffer was added to the cells and incubated at 37° C. or room temperature for 3-16 hours. Assay signal was generated through a single addition of 12.5 or 15 µL (50% v/v) of PathHunter Detection reagent cocktail, followed by one hour incubation at room temperature. Microplates were read following signal generation with a PerkinElmer ENVISION™ instrument for chemiluminescent signal detection. Compound activity was analyzed using CBIS data analysis suite (ChemInnovation, CA). Percentage inhibition was calculated using the following formula: Percent (%) Inhibition=100%×(1−(mean signal of test sample−mean signal of vehicle control)/(mean signal of EC80 control−mean signal of vehicle control)).

Percent (%) inhibition of PPAR-γ was 28.1% at 0.1 µM ROSEMARY EUTECTYS® BLA and 105.9% at 1 µM ROSEMARY EUTECTYS® BLA. See Table 5.

TABLE 5

| Test Solution | % PPAR-γ Inhibition |
|---|---|
| 0.1 µM ROSEMARY EUTECTYS ® BLA | 28.1 |
| 1 µM ROSEMARY EUTECTYS ® BLA | 105.9 |

Example 6

B16 Pigmentation Assay

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay can utilize B16-F1 melanocytes (ATCC), an immortalized mouse melanoma cell line, to analyze the effect of compounds on melanogenesis. The endpoint of this assay can be a spectrophotometric measurement of melanin production and cellular viability. B16-F1 melanocytes, were cultivated in standard DMEM growth medium with 10% fetal bovine serum (Mediatech) at 37° C. in 10% $CO_2$ and then treated for 6 days with solutions containing active ingredients of the formulation of Table 1 above. Following incubation, melanin secretion was measured by absorbance at 405 nm. In a related test, a net 0.3 wt. % solution of a combination of *Pfaffia paniculata* root extract, *Ptychopetalum olacoides* bark/stem extract, and *Trichilia catigua* extract provided a 42% reduction in pigmentation, which corresponds to a significant reduction in melanogenesis.

Example 7

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Antioxidant (AO) Assay:

An antioxidant assay can be performed on skin cells (e.g., epidermal keratinocytes, fibroblasts, and/or dermal endothelial cells) to determine the ability of any one of the active ingredients, combination of ingredients, or compositions having said combinations disclosed in the specification to provide anti-oxidant capacity (TEAC) by inhibiting the oxidation of ABTS® (2,2'-azino-di-[3-ethylbenzthiazoline sulphonate]) to ABTS®.+ by metmyoglobin. The antioxidant system of living organisms can include enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants can provide greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the ingredients in the composition to prevent ABTS oxidation can be compared with that of Trolox, a water-soluble tocopherol analogue, and was quantified as molar Trolox equivalents. Anti-Oxidant capacity kit #709001 from Cayman Chemical (Ann Arbor, Mich. USA) can be used to measure the total anti-oxidant capacity.

Collagen Stimulation Assay:

A collagen stimulation assay can be used to determine the ability of any one of the active ingredients, combination of ingredients, or compositions having said combinations disclosed in the specification to increase expression of procollagen-1, a precursor to collagen. Collagens (types I, II, III, IV and V) can be synthesized as precursor molecules called procollagens. These precursor molecules can contain additional peptide sequences, usually called "propeptides", at both the amino-terminal and the carboxy-terminal ends. During cellular expression and secretion, procollagens can be assembled in the trimeric form and then cleaved at specific N- and C-terminal sites by specific endopeptidases, generating three fragments: procollagen-1 N-terminal propeptide (PINP), Type I collagen, and procollagen-1 carboxy-terminal propeptide (PICP).

The function of the propeptides is to facilitate the winding of procollagen molecules into a triple-helical conformation within the endoplasmic reticulum. The propeptides can be cleaved off from the collagen triple helix molecule during its secretion, after which the triple helix collagens polymerize into extracellular collagen fibrils. Thus, the amount of the free propeptides reflects stoichiometrically the amount of collagen molecules synthesized (a relationship analogous to that between the carboxy-terminal peptide of proinsulin and the endogenously produced insulin). Collagen is an extracellular matrix protein critical for skin structure. Increased synthesis of collagen helps improve skin firmness and elasticity.

Quantitative detection of PICP in fibroblast cell extracts and culture supernatants can be performed with an enzyme immunoassay kit (e.g., Takara #MK101) to assess the effects of the ingredients on the synthesis of PICP in skin. This bioassay can be used to examine effects on the production of procollagen peptide (a precursor to collagen) by human epidermal fibroblasts. The endpoint of this assay can be a spectrophotometric measurement that reflects the presence of procollagen peptide and cellular viability. The assay employs the quantitative sandwich enzyme immunoassay technique whereby a monoclonal antibody specific for procollagen peptide was pre-coated onto a microplate. Standards and samples can be pipetted into the wells and any procollagen peptide present was bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color was developed in proportion to the amount of procollagen peptide bound in the initial step. Color development was stopped and the intensity of the color at 450 nm was measured using a microplate reader.

For generation of samples and controls, subconfluent normal human adult epidermal fibroblasts (Cascade Biologics) can be cultivated in standard DMEM growth medium with 10% fetal bovine serum (Mediatech) at 37° C. in 10% $CO_2$. The cells can be treated with each of the tested ingredients and controls for 3 days. Following incubation, cell culture medium can be collected and the amount of Type I procollagen peptide secretion was quantified using the sandwich enzyme linked immuno-sorbant assay (ELISA) from Takara (#MK101) as explained above.

Elastin Stimulation Assay:

Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers can be monitored in cultured human fibroblasts by staining of cultured human fibroblasts using immuno-fluorescent antibodies directed against elastin by a direct ELISA sandwich method. A Meso Scale Discovery system SECTOR 2400 Imaging system can be used to analyze the results. Changes in elastin secretion and elastin fibers caused by one or more ingredients in the composition can be determined by incubating cultured human fibroblasts with the active ingredient for a period of time before probing the cells or a lysate thereof with antibodies directed against elastin.

Laminin Stimulation Assay:

Laminin is a major protein in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin is a structural glycoprotein located in the DEJ. Together with fibronectin, laminin is considered the glue that holds the cells together, and both are secreted by dermal fibroblasts to help facilitate intra- and inter-cellular adhesion of the epidermal calls to the DEJ.

Laminin secretion can be monitored by quantifying laminin in cell supernatants of cultured human fibroblasts treated for 3 days with culture medium with or without 1.0% final concentration of the test ingredient(s). Following incubation, laminin content can be measured using immunofluorescent antibodies directed against each protein in an enzyme linked immuno-sorbant assay (ELISA).

Matrix Metalloproteinase 1 Enzyme Activity (MMP-1) Assay:

MMPs are extracellular proteases that play a role in many normal and disease states by virtue of their broad substrate specificity. MMP-1 substrates include collagen IV. The Molecular Probes Enz/Chek Gelatinase/Collagenase Assay kit (#E12055), can be used to detect MMP-1 protease activity, and utilizes a fluorogenic gelatin substrate and tests proteolytic cleavage of the substrate by purified MMP-1 enzyme. Upon proteolytic cleavage of the substrate, bright green fluorescence is revealed and can be monitored using a fluorescent microplate reader to measure enzymatic activity. Test materials can be incubated in the presence or absence of the purified enzyme and substrate to determine their protease inhibitor capacity.

Matrix Metalloproteinase 3 and 9 Enzyme Activity (MMP-3; MMP-9) Assay:

MMPs are extracellular proteases that play a role in many normal and disease states by virtue of their broad substrate specificity. MMP-3 substrates include collagens, fibronectins, and laminin; while MMP-9 substrates include collagen VII, fibronectins and laminin. Colorimetric Drug Discovery kits from BioMol International for MMP-3 (AK-400) and MMP-9 (AK-410) can be used to measure protease activity of MMPs using a thiopeptide as a chromogenic substrate (Ac-PLG-[2-mercapto-4-methyl-pentanoyl]-LG-OC2H5)5, 6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm (c=13,600 M-lcm-1 at pH 6.0 and above 7).

Lipoxygenase (LO) Assay:

A lipoxygenase assay can be used to determine the ability of any one of the active ingredients, combination of ingredients, or compositions having said combinations disclosed in the specification to inhibit lipoxygenase (LO) expression. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. An accurate and convenient method for screening lipoxygenase inhibitors can be performed by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of ingredients of the composition to inhibit enzyme activity.

Purified 15-lipoxygenase and test ingredients can be mixed in assay buffer and incubated with shaking for 10 min at room temperature. Following incubation, arachidonic acid can be added to initiate the reaction and the mixtures were incubated for an additional 10 min at room temperature. Colorimetric substrate can be added to terminate catalysis and color progression was evaluated by fluorescence plate reading at 490 nm. The percent inhibition of lipoxyganse activity can be calculated compared to non-treated controls to determine the ability of ingredients of the composition to inhibit the activity of purified enzyme.

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. The bioassay can be used to analyze the effect of ingredients of the composition on the production of TNF-α by human epidermal keratinocytes. The endpoint of this assay can be a spectrophotometric measurement that reflects the presence of TNF-α and cellular viability. The assay can employ the quantitative sandwich enzyme immunoassay technique whereby a monoclonal antibody specific for TNF-α had been pre-coated onto a microplate.

Standards and samples can be pipetted into wells of the microplate and any TNF-α present was bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color developed in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EPILIFE™ standard growth medium (Cascade Biologics) at 37° C. in 5% $CO_2$ can be treated with phorbol 12-myristate 13-acetate (PMA, 10 ng/ml, Sigma Chemical, #P1585-1MG) and of ingredients of the composition or no test ingredient (for negative control) for 6 hours. PMA can be shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Elastase Assay:

ENZCHEK® Elastase Assay (Kit #E-12056) from Molecular Probes (Eugene, Oreg. USA) can be used as an in vitro enzyme inhibition assay for measuring inhibition of elastase activity in the presence of ingredients of the composition. The EnzChek kit can contain soluble bovine neck ligament elastin that is labeled with dye such that the conjugate's fluorescence is quenched. The non-fluorescent substrate can be digested by elastase or other proteases to yield highly fluorescent fragments. The resulting increase in fluorescence can be monitored with a fluorescence microplate reader. Digestion products from the elastin substrate can have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase for a positive control when utilizing the EnzChek Elastase Assay Kit for screening for elastase inhibitors.

Fibronectin Stimulation Assay:

Fibronectin is a major protein in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Fibronectin is a structural glycoprotein located in the DEJ. Together with laminin, fibronectin is considered the glue that holds the cells together, and both are secreted by dermal fibroblasts to help facilitate intra- and inter-cellular adhesion of the epidermal calls to the DEJ.

Fibronectin secretion can be monitored by quantifying fibronectin in cell supernatants of cultured human fibroblasts treated for 3 days with culture medium with or without 1.0% final concentration of the test ingredient(s). Following incubation, fibronectin content can be measured using immuno-fluorescent antibodies directed against each protein in an enzyme linked immuno-sorbant assay (ELISA).

Lysyl Oxidase Assay:

A lysyl oxidase assay can be performed on skin cells (e.g., epidermal keratinocytes, fibroblasts, and/or dermal endothelial cells) to determine the ability of any one of the active ingredients, combination of ingredients, or compositions having said combinations disclosed in the specification to stimulate expression of lysyl oxidase in skin. Lysyl oxidase can catalyze crosslinking of elastin and collagens, thereby providing for a more structurally rigid matrix for skin. By increasing expression of lysyl oxidase, increased cross-linking of elastin and collagens can occur, which can be beneficial in reducing the appearance of fine lines, wrinkles, sagging skin, and/or non-elastic skin.

ORAC Assay:

Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Anti-oxidant Assay kit (#AOX-2)). The Zen-Bio ORAC Anti-oxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Production of Hyaluronic Acid:

Changes in the production of hyaluronic acid (HA) in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Production of Occludin:

Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% $CO_2$ for 24 hours in EPILIFE™ growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$) for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability:

Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Oil Control Assay:

An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a*values of the Minolta Chroma Meter. The a*value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a*values of the Minolta Chroma Meter. The a*value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a2+b2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: Ra=Standardize roughness; lm=the traverse (scan) length; and y=the absolute value of the location of the profile relative to the mean profile height (x-axis).

Production of Filaggrin:

Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200-Mattek EPILIFE™ growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Inhibition of Hyaluronidase Activity:

Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity:

Changes in the activity of PPAR-γ due to each of the active ingredients, any one of the combination of ingredients, or compositions having said combinations disclosed in the specification can be measured. PPAR-γ is a receptor critical for the production of melanin. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine Array:

Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 µl of 100× stock) and 0.1% (10 µl of 100× stock) test compositions are diluted into a final volume of 1 ml EpiLife Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temp. using 70 ml S&S Protein Array Blocking buffer (Whatman Schleicher and Scheull). Blocking buffer is removed and 70 ml of each supernatant sample is added to each array. Arrays are incubated for 3 hours at room temp. with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temp. with gentle agitation. Arrays are washed 3 times with TBS-T. Arrays are incubated with 70 ml of a solution containing streptavidin-Cy5 conjugate for 1 hour at room temp. with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation:

Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 µg/ml bovine brain extract, 1 µg/ml hydrocortisone, and 1 µg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 µl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of reducing dark spots, age spots, and/or unwanted pigmentation of skin, the method comprising topically applying a skin care composition to dark spots, age spots, and/or unwanted pigmentation of skin, the composition comprising an effective amount of niacinamide, phytic acid, *Rosmarinus officinalis* leaf extract, *Chondrus crispus* extract, *Saxifraga sarmentosa* extract, *Carica papaya* (papaya) fruit extract, and *Psidium guajava* fruit extract to reduce dark spots, age spots, and/or unwanted pigmentation of skin.

2. The method of claim 1, wherein the skin care composition further comprises sodium sulfite and sodium metabisulfite.

3. The method of claim 2, wherein the skin care composition comprises an effective amount of sodium sulfite and sodium metabisulfite to reduce dark spots, age spots, and/or unwanted pigmentation of skin.

4. The method of claim 1, wherein the skin care composition comprises 0.1 to 10% by weight of niacinamide, 0.01 to 3% by weight of phytic acid, 0.1 to 5% by weight of *Rosmarinus officinalis* leaf extract, 0.1 to 5% by weight of *Chondrus crispus* extract, and 0.1 to 5% w/w of a combination of *Saxifraga sarmentosa* extract, *Carica papaya* (papaya) fruit extract, and *Psidium guajava* fruit extract.

5. The method of claim 1, wherein the *Rosmarinus officinalis* leaf extract is an extract of deep eutectic solvent comprising lactic acid, betaine, and water, the *Chondrus crispus* extract is an aqueous extract, the *Saxifraga sarmentosa* is a hydroglycolic extract, *Carica papaya* (papaya) fruit is a hydroglycolic extract, and/or *Psidium guajava* fruit extract is a hydroglycolic extract.

6. The method of claim 1, wherein topical application of the composition reduces the overall melanin level of skin.

7. The method of claim 1, wherein topical application of the composition reduces the overall melanin level of skin by at least 5%.

8. The method of claim 1, wherein topical application of the composition reduces the overall melanin level of dark skin by at least 30%.

9. The method of claim 1, wherein the skin is of a person with a brown or black complexion.

10. The method of claim 1, wherein the skin is of a person with a black complexion.

11. The method of claim 1, wherein topical application of the composition inhibits tyrosinase and/or Peroxisome Proliferator-Activated Receptor Gamma (PPAR-γ) activity of the skin.

12. The method of claim 1, wherein the skin care composition further comprises glycerin and caprylyl/capryl glucoside.

13. The method of claim 1, wherein the skin care composition further comprises an effective amount of *Pfaffia paniculata* root extract, *Ptychopetalum olacoides* bark/stem extract, and *Trichina catigua* extract to reduce dark spots, age spots, and/or unwanted pigmentation of skin.

14. A skin care composition comprising an effective amount of niacinamide, phytic acid, *Rosmarinus officinalis* leaf extract, *Chondrus crispus* extract, *Saxifraga sarmentosa* extract, *Carica papaya* (papaya) fruit extract, and *Psidium guajava* fruit extract to reduce dark spots, age spots, and/or unwanted pigmentation of skin.

15. The composition of claim 14, wherein the skin care composition further comprises sodium sulfite and sodium metabisulfite.

16. The composition of claim 15, wherein the skin care composition comprises an effective amount of sodium sulfite and sodium metabisulfite to reduce dark spots, age spots, and/or unwanted pigmentation of skin.

17. The composition of claim 14, comprising 0.1 to 10% by weight of niacinamide, 0.01 to 3% by weight of phytic acid, 0.1 to 5% by weight of *Rosmarinus officinalis* leaf extract, 0.1 to 5% by weight of *Chondrus crispus* extract, 0.1 to 5% w/w of a combination of *Saxifraga sarmentosa* extract, *Carica papaya* (papaya) fruit extract, and *Psidium guajava* fruit extract, and further comprising 0.1 to 5% by weight of undecylenoyl phenylalanine.

18. The composition of claim 14, wherein the *Rosmarinus officinalis* leaf extract is an extract of deep eutectic solvent comprising lactic acid, betaine, and water, the *Chondrus crispus* extract is an aqueous extract, the *Saxifraga sarmentosa* extract is a hydroglycolic extract, the *Carica papaya* (papaya) fruit is a hydroglycolic extract, and the *Psidium guajava* fruit extract is a hydroglycolic extract.

19. The composition of claim 14, wherein the composition further comprises glycerin and caprylyl/capryl glucoside.

20. The composition of claim 14, wherein the composition further comprises an effective amount of *Pfaffia paniculata* root extract, *Ptychopetalum olacoides* bark/stem extract, and *Trichina catigua* extract to reduce dark spots, age spots, and/or unwanted pigmentation of skin.

* * * * *